United States Patent [19]
Kupiecki et al.

[11] Patent Number: 5,603,991
[45] Date of Patent: Feb. 18, 1997

[54] METHOD FOR COATING CATHETER LUMENS

[75] Inventors: David Kupiecki, Cupertino; Thuzar K. Han, Fremont, both of Calif.

[73] Assignee: Target Therapeutics, Inc., Fremont, Calif.

[21] Appl. No.: 539,902

[22] Filed: Sep. 29, 1995

[51] Int. Cl.⁶ .................................................. C08F 2/48
[52] U.S. Cl. ............... 427/508; 427/230; 427/393.5; 427/430.1; 427/512; 427/558; 427/559; 427/581
[58] Field of Search .................................. 427/508, 512, 427/558, 559, 581, 230, 393.5, 430.1

[56] References Cited

U.S. PATENT DOCUMENTS

| | | | |
|---|---|---|---|
| 3,556,874 | 3/1971 | Shepherd et al. | 128/349 |
| 3,861,396 | 1/1975 | Vaillancourt et al. | 128/350 R |
| 4,417,892 | 11/1983 | Meisch | 604/323 |
| 4,739,768 | 4/1988 | Engelson | 128/772 |
| 4,876,126 | 10/1989 | Takemura et al. | 428/35.7 |
| 4,884,579 | 12/1989 | Engelson | 128/658 |
| 4,898,591 | 2/1990 | Jang et al. | 604/282 |
| 4,994,047 | 2/1991 | Walker et al. | 604/264 |
| 5,047,045 | 9/1991 | Arney et al. | 606/194 |
| 5,124,129 | 6/1992 | Riccitelli et al. | 422/56 |
| 5,201,724 | 4/1993 | Hukins et al. | 604/265 |
| 5,281,203 | 1/1994 | Ressemann | 604/164 |
| 5,300,032 | 4/1994 | Hibbs et al. | 604/164 |
| 5,336,178 | 8/1994 | Kaplan et al. | 604/53 |

*Primary Examiner*—Bernard Pianalto
*Attorney, Agent, or Firm*—Morrison & Foerster

[57] ABSTRACT

This invention is in the general field of surgical instruments and, in particular, catheters. Specifically, it relates to procedures for coating the interior surfaces of surgical devices with a cross-linkable lubricious polymer, preferably one which is hydrophilic. These catheters may be variously used in cardiovascular and endovascular procedures to deliver diagnostic, therapeutic, or vaso-occlusive agents or devices to a target site within a human or animal body and to catheters used to guide other catheters to a particular site in that body. The interior of the catheters are coated using the noted procedure in such a way that the interior is exceptionally slippery and very durable.

11 Claims, 3 Drawing Sheets

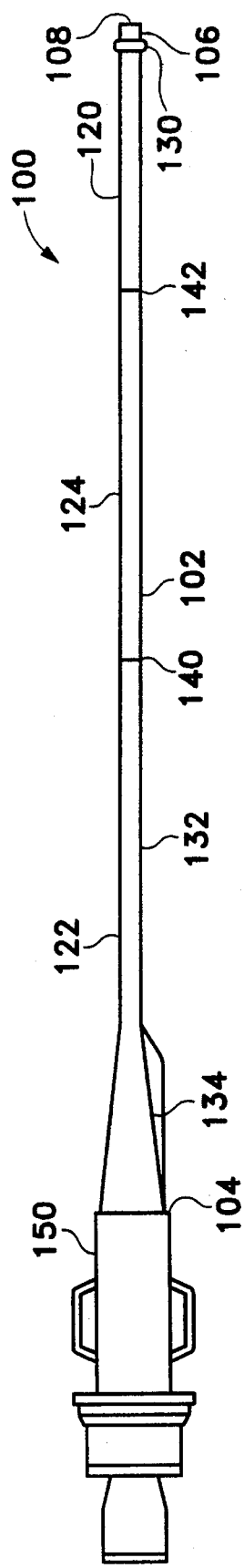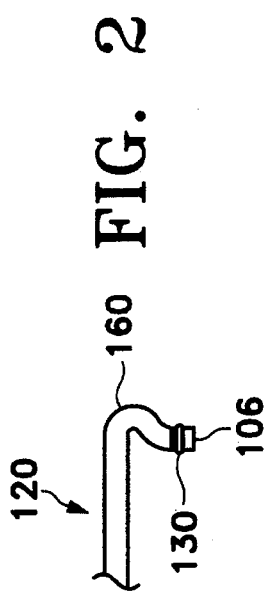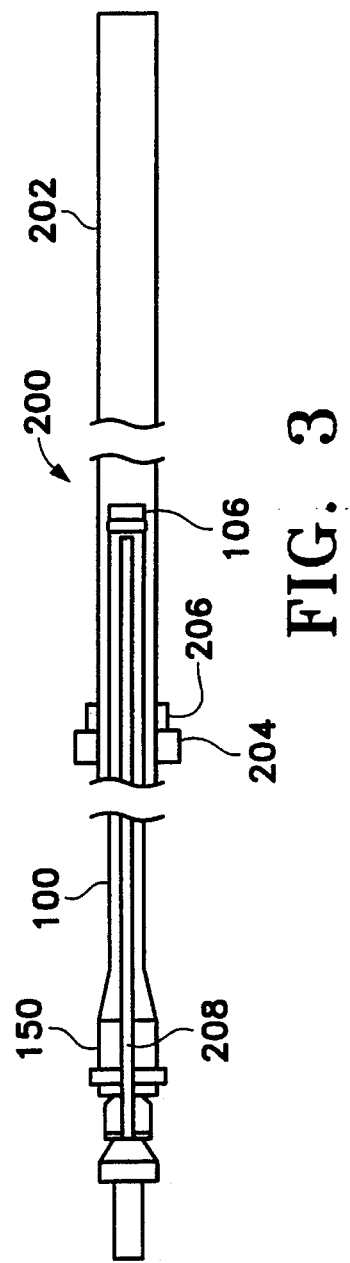

METHOD FOR COATING CATHETER LUMENS

FIELD OF THE INVENTION

This invention is in the general field of surgical instruments and, in particular, catheters. Specifically, it relates to procedures for coating the interior surfaces of such catheters with a cross-linkable lubricious polymer, preferably one which is hydrophilic. These catheters are at least partially made of polymeric materials which are appropriately transparent to the passage of uv-radiation so to allow curing or cross-linking of the lubricious polymer precursor as an interior layer in-situ. The resulting catheters may be variously used in cardiovascular and endovascular procedures to deliver diagnostic, therapeutic, or vaso-occlusive agents or devices to a target site within a human or animal body and to catheters used to guide other catheters to a particular site in that body.

BACKGROUND OF THE INVENTION

Catheters may be used to deliver diagnostic or therapeutic agents and devices to internal target sites that can be accessed through the circulatory or other system. There are a number of general approaches for placing catheters within vessels in the body to reach target sites that are difficult to access. In one technique, a torqueable guidewire is introduced into the vasculature and, using radiography to monitor its advance through the body's passageways, is rotated as necessary to allow the guidewire's bent guide tip to follow a chosen route (when a choice of pathways is found) and is advanced towards the target site. At chosen intervals during the guidewire's advancement, the catheter is slid along the guidewire until the distal end of the catheter approaches the distal end of the guidewire. This procedure is repeated until the distal end of the catheter is positioned at the target site. An example of this technique is described in U.S. Pat. No. 4,884,579. This is a widely accepted and respected method for approaching target sites in complicated areas of the vasculature. It, however, has the drawback of being somewhat time-consuming due to the necessity of rotating and advancing the guidewire and catheter through the vasculature.

A second technique for advancing a catheter to a target site is to use the blood flow as the motive force in placing the distal end of the catheter at the desired target site. Such methods often employ a highly flexible catheter having an inflatable, but pre-punctured balloon at its distal end. In use, the balloon is partially inflated, and carried by blood flow into the target site. During placement, the balloon is continually inflated to replenish fluid leaking from the balloon. This technique, too, has drawbacks including the fact that at least the distal portion of the catheter is so floppy that it cannot be pushed without buckling. Instead, the catheter must be advanced using injected fluid to inflate the balloon to propel the catheter to the target site. There is the additional risk of rupturing a vessel with a balloon that has been overinflated.

In order to address some of the above described problems, another approach has involved the use of flexible catheters having extremely flexible distal portions that can be directed to a target site using the blood flowing to that site as the motive force but without the use of balloons on the distal catheter tip. These flow-directed catheters have the advantage of being quite fast in that they are able to access remote portions of the body very quickly. They carry the obvious limitation that the catheter distal tip can only go where the blood flow is the highest. Furthermore, the catheters often are limited in the size of the "load" carried to the selected site. Said another way, balloon-less flow-directed catheters may be a marginal choice if a larger embolic coil or large diameter particle is to be delivered to the selected site.

In comparison to flow-directed catheters, over-the-wire catheters having variable stiffness (although quite strong and able to deliver embolic coils and large diameter particles through their large lumen) are comparatively quite slow in time of access. Friction with the interior of the guide catheter or the vessel path considerably slows the procedure time. The time needed to push the catheter over the guidewire is often lengthy simply because of friction with the guidewire. Over-the-wire catheters have advantages in that they can be directed to portions of the vasculature inaccessible to flow-directed catheters and they are compatible with a much broader selection of embolic devices. Lowering the resistance of the over-the-wire catheter to improve its interior or exterior lubricity and thereby, to allow improved access time to remote body sites, forms a further aspect of this invention.

This invention is, generically, a method for coating the interior of a catheter. These catheters typically have portions of differing flexibility and, so, are suitable for the delivery of diagnostic, therapeutic, or vaso-occlusive agents or devices to potentially remote portions of the vascular system or other systems of open lumen within the body. A thin coating of a lubricious polymer is applied at least to the interior of the catheter and optionally to the outside of the catheter. The preferred coating is quite slippery and is very durable.

This method of coating the interior of catheters with lubricious hydrophilic polymers involves the choice of specific uv-light transmissible polymeric tubing and desirably involves the use of particular method steps in which the lubricious polymeric precursors are carefully applied to the polymeric catheter substrates, any carrier solvent removed, and the precursors cured in situ by application of uv radiation to the exterior of the catheter.

There are a variety of prior art documents showing the use of hydrophilic polymeric coatings on the surfaces of catheter devices.

Typical of devices having such coatings are those described in U.S. Pat. No. 3,556,874 to Shepherd et al.; and U.S. Pat. No. 3,861,396 to Vaillancourt, et al.; and U.S. Pat. No. 4,417,892 to Meisch; and U.S. Pat. No. 4,876,126 to Takemura, et al.; and U.S. Pat. No. 4,898,591 to Jang, et al.; and U.S. Pat. No. 4,994,047 to Walker et al.; and U.S. Pat. No. 5,300,032 to Hibbs, et al. None of these patents show the use of ultraviolet light for the curing of hydrophilic coatings on the interior of vascular catheters or catheter sections. Most of these documents show the cross-linking of the hydracoat polymers with irradiation or heat or through the use of cross-linking agents mixed with a polymer precursor.

other devices made up of tubing having lubricious surface, not necessarily bonded in situ, are found in the following: U.S. Pat. No. 5,047,045 to Arney, et al.; to U.S. Pat. No. 5,201,724 to Hukins, et al.; to U.S. Pat. No. 5,281,203 to Ressemann and in U.S. Pat. No. 5,336,168 to Kaplan, et al.

An interesting medical device—a carbon dioxide indicator used as a section of an endotracheal tube is shown in U.S. Pat. No. 5,124,129 to Riccitelli, et al. That device is a tube having a pH-sensitive dye suspended in a hydrophilic polymer matrix placed on the inside of an indicator tube or connector. When the pH-sensitive dye changes color due to the presence of $CO_2$ in moisture in exhaled air, the color change is visible from outside of the device due to the fact that the walls of the device are made of a transparent polymer. Ultraviolet light is used to cross-link the polymers in the color-bearing matrix and render the resulting polymer insoluble in water.

None of these references show the use of uv-transparent, polymeric, flexible tubing so to allow the curing of a hydrophilic or lubricious covering on the interior of that tubing.

SUMMARY OF THE INVENTION

This invention is a method for coating the interior of a catheter or section of a catheter. The product catheter may be used for placement within a tortuous, small vessel pathway and a method for delivery of an agent or device to a target site. The coating is very slippery and quite durable. The catheter may be directed to the target site either by means of the blood flow to that site or by the use of a guidewire. The product catheter has an elongate tubular body having proximal and distal ends and a lumen extending between the ends through which the diagnostic, therapeutic, or vaso-occlusive agent or device is delivered. Where appropriate, the lumen may be used for passage of a guidewire. The catheter may have a balloon located near its distal end.

Desirably, the product elongate tubular body may be formed of (a) a relatively stiff and, perhaps, tapered proximal segment, (b) a relatively flexible distal segment, and (c) one or more transition or intermediate sections between the proximal and distal segments that are less flexible than the distal segment but more flexible than the proximal segment. The interior of at least the distal segment and, desirably, the transition segments of the catheter are treated with a lubricious, polymeric material using the procedure of this invention. The proximal section of the catheter may also be so treated. If so desired, all or part of the exterior of the catheter may be coated with the lubricious polymers.

The procedure may also be used to produce a flow-directed catheter. In that variation, the elongate tubular body is typically formed of a relatively stiff tapered proximal segment, a relatively flexible and strong distal segment, and a transition section between the proximal and distal segments that is less flexible than the distal segment but more flexible than the proximal segment.

The procedure may also be used to produce a guiding catheter that has been coated on its interior. These catheters are typically used in conjunction with vascular access catheters such as the guidewire-directed and flow-directed catheters and balloon catheters noted just above. The guiding catheters have inside diameters suitably sized to allow those other catheters to pass through their lumen. Such a guiding catheter may have a fairly stiff proximal section, often with a shorter straight section positioned near the distal section and often having significantly softer sections placed at the distal region and distal end. These catheters are used for quick placement, in the body, of the flow-directed or guidewire-directed catheter to a point where they are most efficient or, said another way, they act as platforms for the microcatheters or flow-directed catheters.

The interior of the catheter bodies are coated with hydrophilic polymeric materials by a method involving application of the polymer from a dilute polymer or oligomer solution desirably followed by simultaneous solvent removal and curing of the applied precursor. The sections of the catheters to be so coated are formulated with ultraviolet light transparent/translucent polymeric tubing allowing curing of the coating placed on the catheter interior by passage of the uv-light through the walls. The uv-radiation cures the previously applied interior coating and may also be used to cure a coating applied to the exterior of the catheter. Multiple coatings of the polymeric material may be useful.

BRIEF DESCRIPTION OF THE DRAWINGS

FIG. 1 is a diagram that shows an infusion catheter constructed according to a preferred embodiment of the present invention.

FIG. 2 is a diagram that shows the distal end on one embodiment of a flow-directed infusion catheter of the present invention in which the distal end is formed in an "S" shaped configuration.

FIG. 3 is a diagram showing a flow-directed infusion catheter, stylet, and guiding catheter assembly.

DESCRIPTION OF THE INVENTION

Figure 4:
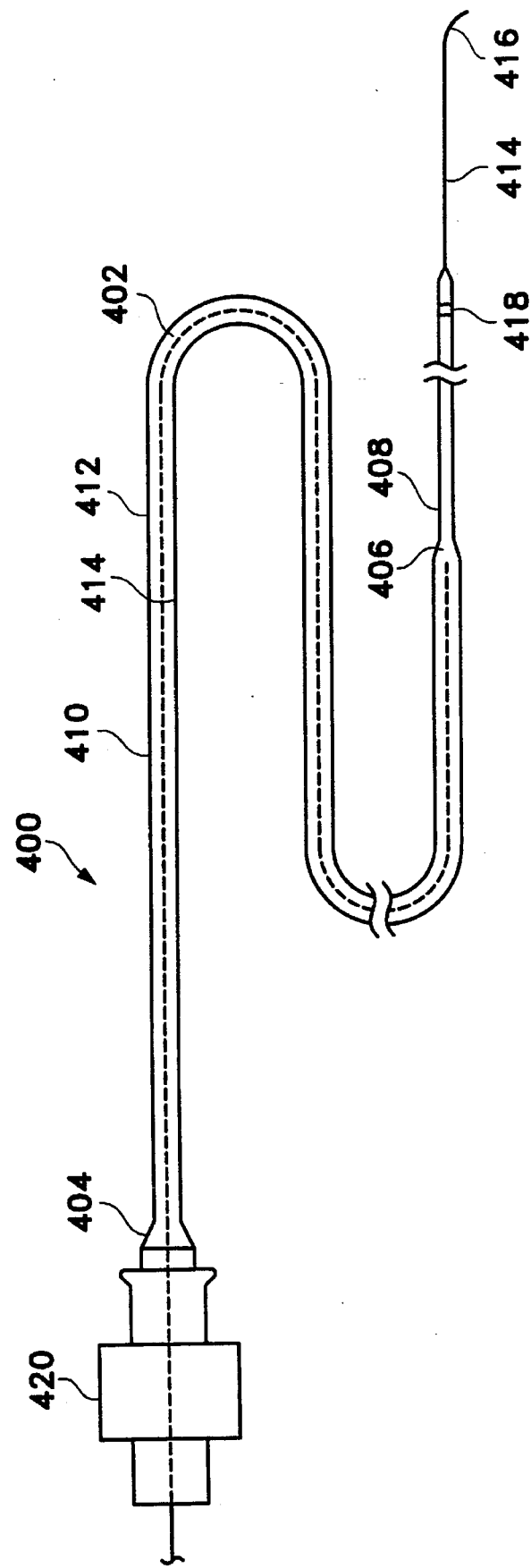
FIG. 4 is a side view of a typical catheter assembly according to this invention adapted for use with a guidewire.

This invention is a method for coating the interior of a variety of catheters with a lubricious polymer, which coating is cross-linked in situ and covalently bonded to the interior of the catheter using irradiation. Central to this invention is the use of polymers in at least a portion of the substrate catheter which are transparent or translucent to uv-radiation.

The substrates may be portions or sections of catheters or complete catheter assemblies.

One desirable variation of suitable catheters, optionally including a guidewire, has discrete sections of varying flexibility. Desirably, the catheter has a relatively stiff proximal section and a less stiff mid-section. For devices intended for use as flow-directed catheters, the distal end section is quite flexible; for devices intended for use with guidewires, the distal end section need not be quite as flexible since it need only follow the path of the guidewire without substantial disturbance of that pre-determined path. The various sections of the catheter may also be of variable flexibility or the entire length of the catheter may have a variable flexibility.

At least some portion of the interior portion of the catheter is coated with a polymeric material according to the inventive process to increase its lubricity and to minimize the friction seen by the guidewire or by mechanical therapeutic or vaso-occlusive devices as they move through the catheter lumen. The mid exterior or transition section of the catheter may also be coated with the polymeric material. The proximal section exterior may also be coated although, most desirably, a small proximal end portion is left uncoated for increased control.

Another variation of a suitable substrate is a flow-directed catheter. In a flow-directed catheter, the elongate tubular body is typically formed of a relatively stiff tapered proximal segment, a relatively flexible and strong distal segment, and one or more transition sections between the proximal and distal segments that are less flexible than the distal segment but more flexible than the proximal segment.

A further variation is a guiding catheter that has been coated on its interior as described herein. These catheters are typically used in conjunction with vascular access catheters such as the guidewire-directed and flow-directed catheters noted just above. The guiding catheters have inside diameters suitably sized to allow those other catheters to pass through their lumen. Such a guiding catheter may have a fairly stiff proximal section, often with a shorter straight section positioned near the distal section and often having significantly softer sections placed at the distal region and end. These catheters are used for quick placement in the body of the flow-directed or guidewire-directed catheter to a point where they are most efficient.

Coatings

Particularly suitable as coatings in the catheter assembly of this invention are polymers or oligomers of monomers selected from ethylene oxide and its higher homologs including up to 6 carbon atoms; 2-vinyl pyridine; N-vinylpyrrolidone; polyethylene glycol acrylates such as monoalkoxy polyethylene glycol mono(meth)acrylates, including mono-methoxy triethylene glycol mono (meth) acrylate, mono-methoxy tetraethylene glycol mono (meth) acrylate, polyethylene glycol mono (meth) acrylate; other hydrophilic acrylates such as 2-hydroxyethylmethacrylate, glycerylmethacrylate; acrylic acid and its salts; acrylamide and acrylonitrile; acrylamidomethylpropane sulfonic acid and its salts, cellulose, cellulose derivatives such as methyl cellulose ethyl cellulose, carboxymethyl cellulose, cyanoethyl cellulose, cellulose acetate, polysaccharides such as amylose, pectin, amylopectin, alginic acid, and cross-linked heparin; maleic anhydride; aldehydes; etc. These monomers may be formed into homopolymers or block or random copolymers. The use of oligomers of these monomers in coating the catheter for further polymerization is also an alternative. Preferred monomers include ethylene oxide; 2-vinyl pyridine; N-vinylpyrrolidone and acrylic acid and its salts; acrylamide and acrylonitrile each polymerized (with or without substantial cross-linking) into homopolymers, or into random or block copolymers.

Additionally, hydrophobic monomers may be included in the polymeric coating material in an amount up to about 30% by weight of the resulting copolymer so long as the hydrophilic nature of the resulting copolymer is not substantially compromised. Suitable monomers include ethylene, propylene, styrene, styrene derivatives, alkylmethacrylates, vinylchloride, vinylidenechloride, methacrylonitrile, and vinyl acetate. Preferred, because of their propensity for ease of linkage to the typical polymeric catheter substrates, are ethylene, propylene, styrene, and styrene derivatives.

Polymers or oligomers applied using the procedure described below are activated or functionalized with photoactive groups to permit reaction of the polymers or oligomers with the underlying polymeric surface. Suitable activation groups include benzophenone, thioxanthone, and the like; acetophenone and its derivatives specified as:

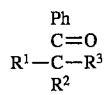

where

R$^1$ is H, R$^2$ is OH, R$^3$ is Ph; or

R$^1$ is H, R$^2$ is an alkoxy group including —OCH$_3$, —OC$_2$H$_3$, R$^3$ is Ph; or R$^1$=R$^2$=an alkoxy group, R$^3$ is Ph; or R$^1$=R$^2$=an alkoxy group, R$^3$ is H; or R$^1$=R$^2$=Cl, R$^3$ is H or Cl.

Other known activators are suitable.

The polymeric coating may then be linked with the substrate using the techniques described herein. The chosen activators are activated by ultraviolet light.

The polymeric coating may be applied to the exterior of the catheter body or other polymeric substrate by any of a variety of methods, e.g., by spraying a solution or suspension of the polymers or of oligomers of the monomers onto the catheter or by dipping the catheter into the solution or suspension (after sealing the open ends, if so desired). Initiators may be included in the solution or applied in a separate step. The catheter may be sequentially or simultaneously dried to remove solvent after application of the polymer or oligomer to the exterior of the polymeric body and cross-linked.

PROCEDURE FOR INSIDE DIAMETER COATING

The polymeric coating may be applied to the interior of the catheter by use of pressure forcing the precursor fluid through that interior. The polymeric precursor fluid may be drawn into the interior of the catheter by gravity or by vacuum. Because of the difficulty of achieving a reasonably smooth and even layer within that interior, the polymer precursor solution used for the catheter interior desirably is cured by uv-radiation. This is so because the polymer precursor solution should be physically stable when cross-linked. In some instances, this would mean that the solvent has been substantially removed from the layer coating the interior of the catheter. In other instances, a fluid coating may be present on the interior, but it typically must have had the majority of the solvent removed to allow sufficient concentration of the photoactive groups to mandate the binding of the precursor to the inner catheter lumen. Thin solutions are very, very difficult to polymerize.

The solution or suspension should be quite dilute since only a very thin layer of polymer is to be applied either to the interior or to the exterior of the catheter. We have found that an amount of oligomer or polymer in a solvent of between 0.25% and 5.0% (wt), preferred is 0.5 to 2.5% (wt), is excellent for thin and complete coverage of the resulting polymer. Preferred solvents for this procedure when using the preferred polymers and procedure are water, low molecular weight alcohols, especially methanol, propanol, isopropanol, ethanol, and their mixtures and ethers. Other water miscible solvents, e.g., tetrahydrofuran, methylene dichloride, methylethylketone, dimethylacetate, ethyl acetate, dimethyl acetamide, etc., are suitable for the listed polymers and must be chosen according to the characteristics of the polymer; they should be polar because of the hydrophilic nature of the polymers and oligomers but, because of the reactivity of the terminal groups of those materials, known quenching effects caused by oxygen, hydroxyl groups, and the like must be recognized by the user of this process when choosing polymers and solvent systems.

Particularly preferred as coatings for the catheter bodies discussed below are physical mixtures of homo-oligomers of at least one of polyethylene oxide; poly 2-vinyl pyridine; polyvinylpyrrolidone, polyacrylic acid, polyacrylamide, and polyacrylonitrile.

Exterior Coating

When applying a polymeric coating to the exterior of the catheter, the catheter bodies or substrates are preferably sprayed or dipped, dried, and irradiated to produce a polymerized and cured and bonded polymeric skin of the noted monomers or oligomers. The exterior lubricious hydrophilic coating may be produced using generally sequential solvent removal and cross-linking operations. The coating is applied at a rate allowing "sheeting" of the solution, e.g., formation of a visibly smooth layer without "runs". In a dipping operation for most polymeric substrates noted below, the optimum coating rates generally are a linear removal rate between 0.25 and 2.0 inches/sec, preferably 0.5 and 1.0 inches/sec.

The solvent evaporation operations may be conducted using a heating chamber suitable for maintaining the surface at a temperature between 25° C. and the glass transition temperature ($T_g$) of the underlying substrate. Preferred temperatures are 30° C. to 75° C.

Ultraviolet light sources may also be used to cross-link the polymer precursors onto the substrate polymeric device. Movement through an irradiation chamber having an ultraviolet light source at 90–375 nm (preferably 300–350 nm) having an irradiation density of 50–1200 mW/cm$^2$, preferably 50–300 mW/cm$^2$, most preferably 150–250 mW/cm$^2$ for a period up to seven seconds is desired. Passage of a catheter through the chamber at a rate of 0.1 to 2.0 inches/second (0.5 to 1.0 inches/second) in a chamber having three to nine inches length is suitable.

In sum, the process preferably involves the substantive steps of creating a coating of substantial uniformity, drying, and then curing the coating using ultraviolet radiation to produce a coating which is covalently bonded to the substrate.

Exceptional durability of the resulting exterior coating is produced by repetition of the dipping/solvent removal/irradiation steps up to five times. Preferred are two to four repetitions.

Interior Coating

As was the case with applying the polymer precursor to the exterior of the catheter, the solution or suspension of the polymer precursor should be quite dilute. The amount of oligomer or polymer in a solvent may desirably be between 0.10% and 5.0% (wt), preferred is 0.10% to 2.5% (wt) to assure coverage of the interior surface of the catheter. A small amount of a flow additive is also desirable. It must be remembered that the interior diameter of many catheters is perhaps as small as 0.008 inches.

Solvents suitable for this operation are the same as those listed for exterior coating although there is a preference for low molecular weight solvents to lower the overall viscosity of the precursor solution.

Similarly, the polymer precursors listed for use as exterior catheters are also suitable for interior coating.

As was noted above, the coating is preferably applied using a pressurized, gravity fed, or vacuum propelled source to pass the precursor solution through the catheter. The catheters are generally oriented vertically. Once the catheter is filled. The solution is then expressed to allow the solution to coat the interior but not to form plugs or the like. The optimum rate for allowing the precursor fluid to drop in the catheter lumen is generally in the range of 0.1 to 0.75 in/sec, preferably 0.2 to 0.4 in/sec., and most preferred 0.08 to 0.16 in/sec.

Heated air (e.g., at 100°–350° F.) may be introduced into the region of the catheter perhaps with added direct heat, to remove the solvent, and leave a thin coat behind. If a uniform coating is necessary, this step must be carried out at a proper and multi-step low volume flow rate to form that uniform coating prior to the irradiation step.

The catheter body is then exposed to a uv source for a period of time sufficient for cross-linking the polymer.

The steps of coating, dying, and cross-linking may be repeated for two or more iterations.

Polymeric Substrates

Materials which are suitable for the tubing walls of the catheter section include polymeric compositions such as low density polyethylene, linear low density polyethylene, high density polyethylene, polyurethane, various block copolymers containing polyamides, polyvinyl chloride, and silicones, or blends of the above. The compositions must be sufficiently clear to allow a substantial portion, e.g., greater than about 25%, of ultraviolet light to pass through. They should be substantially clear although some amount of coloring is permitted.

Physical variations

FIG. 1 shows an infusion catheter (100) coated using the invention. The catheter (100) has an elongate tubular body (102) with proximal (104) and distal (106) ends and an open inner lumen (108) extending between the ends. The elongate tubular body (102) has three segments; a relatively flexible and strong distal segment (120), a relatively stiff tapered proximal segment (122) and a transition section or segment (124) between the proximal and distal segments that is less flexible than the distal segment (120) but more flexible than the proximal segment (122).

The elongate tubular body (102) has a strong distal segment (120) which is desirably "relatively flexible" such that the catheter can easily navigate a tortuous vessel pathway. By "relatively flexible" is meant that, at 10 cm., a force of about $1 \times 10^{-4}$ pounds corresponds to a deflection of the material that is 10° from horizontal, or only about $5 \times 10^{-4}$ pounds of force to deflect the material about 80° from horizontal. By "relatively strong" is meant that the material has a burst pressure of greater than 195 psi, more preferably, the burst pressure is between about 195 and 220 psi.

The flexible distal segment (120) has an open end which allows for the infusion of diagnostic, therapeutic, or vasoocclusive agents into the target site. When the catheter is a flow-directed infusion catheter, the flexible distal segment (120) preferably is made of a polymer that is springy, biologically compatible, and which passes at least a sufficient amount of uv-light to its interior lumen so to allow the cross-linking of the polymeric precursors discussed above. Such polymers include materials such as low density polyethylene, polyurethane, a block copolymer of polyamide, polyvinyl chloride, or silicone, or blends of the above. Critical to the invention is the requirement that the polymer, as configured in the elongate member, is reasonably translucent to uv-radiation of a wavelength suitable for such cross-linking reaction. For instance, the transmissivity of the polymer should allow 25% transmittance in the 300–350 nm range at 10–250 mw/cm$^2$. As a practical matter, many polymeric compositions which pass uv-radiation are also quite clear, hence passing white light.

The flexible distal segment (120) may carry one or more radiopaque bands (130). In some instances, the segment (120) may be doped with a radiopaque material such as barium sulfate, bismuth trioxide, bismuth carbonate, tungsten, tantalum or the like so that the location of the distal region of the catheter within the vessel may be visualized radiographically. However such doping interferes with the passage of uv-radiation during the curing step and hence is not preferred. The distal segment (120) typically makes up between about 5 and 25% of the total length of the tubular member and is between about 5 and 40 cm long, preferably between about 10 and 20 cm long. The inner diameter of the distal segment (120) may be between about 0.25 and 0.50 mm, more preferably between about 0.25 and 0.35 mm. The outer diameter of the distal segment may be between about 0.50 and 0.80 mm, more preferably between about 0.60 and 0.70 mm. The wall thickness of the distal segment 120 is between about 0.1 and 0.3 mm.

The proximal segment (122) of the elongate tubular body (102), when used as a flow-directed infusion catheter, is relatively stiff so that it can be easily pushed and thus eliminate need for guidewire support. The proximal segment (122) may be made of a polymeric or metallic material that is relatively stiff and biologically compatible, e.g., high density polyethylene, polypropylene, polyamides such as Nylons, polyurethane, polyimides, polyvinyl chloride, polysulfones, polyfluorocarbons, polyethylene terephthalate, their mixtures, copolymers; or polyester elastomers or a braided shaft (a polymer outer core with a metallic mesh inner core). As was noted above, should this section of the catheter be coated using the procedure specified herein, the polymers must allow the passage of uv-radiation. The proximal segment (122) may comprise a tapered proximal section (134) for attachment to the proximal end fitting (150) and a distal section (132). The proximal section (134) of proximal segment (122) may make up between about 60% and 80% of the total length of the tubular member (102) and typically is between about 90 and 130 cm long, preferably between about 100 and 120 cm long. The largest inner diameter of the proximal section (134), measured at the proximal end (104) of the tubular member (102), is often between about 0.40 and 0.60 mm, more preferably between about 0.45 and 0.55 mm. The outer diameter of the proximal section (134) at the proximal end (104) of the tubular member (102) is between about 0.8 and 1.2 mm. The wall thickness of the proximal section (134) of proximal segment (122) is between about 0.1 and 0.4 mm, more preferably between about 0.2 and 0.3 mm The distal section (132) of proximal segment (122) makes up between 10 and 20% of the total length of the tubular body (102) and is between about 20 and 40 cm long, preferably between about 20 and 30 cm long. The inner diameter of the distal section (132) of proximal segment (122) may be between about 0.20 and 0.50 mm, more preferably between about 0.25 and 0.35 mm. The outer diameter of the distal section (132) of proximal segment (122) is between about 0.60 and 0.90 mm, more preferably between about 0.60 and 0.70 mm. The wall thickness of the distal section (134) of proximal segment (122) is typically between about 0.1 and 0.3 mm.

The transition section (124) of the elongate tubular body (102) is less stiff than the proximal segment (122) but more stiff than the distal segment (120). A suitable material that is biologically compatible is a polymer such as polyurethane, a block copolymer of polyamide, polyvinyl chloride or silicone with greater durometer reading (i.e. that is stiffer) than the flexible distal segment (120). The transition section (124) may be radiopaque and thus observable in the event that the catheter becomes lodged in a particular portion of the vasculature or if it buckles. The polymeric material may be doped with a radiopaque material such as barium sulfate, bismuth carbonate, bismuth trioxide, tungsten, tantalum or the like. Bismuth trioxide is not always color-stable when exposed to ultraviolet light and may not be a wise choice if color-fastness is a desirable choice. The transition section (124) may make up between about 10 and 20% of the total length of the tubular member (102) and is between about 20 and 40 cm long, preferably between about 25 and 35 cm long. The transition section (124) may be of constant diameter or may be tapered. The inner diameter of the transition section (124) may be between about 0.20 and 0.50 mm, more preferably between about 0.20 and 0.35 mm. The outer diameter of the transition section (124) may be between about 0.50 and 0.90 mm, more preferably between about 0.60 and 0.70 mm. The wall thickness of the transition section (124) may be between about 0.1 and 0.3 mm.

The proximal segment (122), transition section (124), and distal segment (120) are joined at junctions (140) and (142), respectively. The junctions may be formed by flaring, overlapping, and heat fusing the materials of the proximal segment (122) and transition section (124) and the transition section (124) and distal segment (120). Other methods for forming the junction, e.g., heat welding, solvent welding, etc. are also suitable. The distal segment (120), transition section (124) and distal section (132) of proximal segment (122) may all have approximately the same outside diameter or the transition section (124) and the distal section (132) of the proximal segment (122) may be tapered.

A standard proximal end fitting (150) may be attached to the proximal end (134) of the proximal segment (122) often by gluing or by heat fusion with reinforcing tubing.

The lumen of these catheter embodiments extends from the distal end (108), through distal section (120) through midsection (124) and through proximal section (122). It is this lumen which is to be coated with the polymeric material discussed herein to improve its lubricity.

FIG. 2 shows an embodiment of the distal segment (120) of the catheter where the tip (160) of the catheter is preshaped by heating, e.g., with steam, so that the distal end (106) can point towards the wall of the vessel rather than in the direction of blood flow to increase the ease of manipulation through a tortuous vessel pathway. The particular embodiment shown is an "S" shape, but the tip may be any shape that allows for access to the particular vasculature being treated. One additional shape is that of a hockey stick. In this way, if the catheter becomes lodged against the vessel wall, the infusion of liquid through the catheter propels the distal end (106) of the catheter away from the vessel wall. Since the stiff proximal segment (122) is pushed, the distal segment (120) will be carried by the blood flood to the target site.

The catheters described above are useful in delivering diagnostic, therapeutic, or vaso-occlusive agents and devices to deep tissue, usually without need for a guidewire.

FIG. 3 shows a catheter assembly (200) for placing the infusion catheter (100) at the target site. An appropriate guiding catheter (202) is inserted into the vasculature using standard placement techniques. A rotating hemostatic valve (204) may be utilized by connection to the guiding catheter luer adapter (206). The guiding catheter (202) is continuously flushed with saline. The thumb-screw of the valve (204) is opened and the infusion catheter (100) is inserted through the rotating hemostatic valve (204). Optionally, as shown in FIG. 3, a Teflon-coated stainless steel stylet (208) is first inserted into the flow-directed infusion catheter (100) in order to prevent kinking of the infusion catheter (100) within the valve (204). The distal end (106) of the infusion catheter (100) is advanced proximal to the tip of the guiding catheter (202). The stylet (208) is then removed from the infusion catheter (100). Once the stylet (208) is removed, the infusion catheter (100) is pushed out of the guiding catheter (202). The flow-directed infusion catheter (100) is gently guided by the flow of blood in the vasculature to the target site. Optionally, gentle pushing and pulling and injection of saline or contrast medium through the catheter lumen (108) may aid in the placement of the catheter at the target site.

Once at the target site, the desired agent is injected. Such agents may include radiopaque agents for viewing blood vessel anatomy and blood flow characteristics in the target region, vaso-occlusive agents which can be used to produce small-artery vaso-occlusion in the tissue region supplied by the target vessel, and pharmacological agents, such as antitumor drugs or sclerosing agents such as alcohols, which are effective against identified disease states at the target site. Vaso-occlusive agents useful in the treatment of arteriovenous malformations include polymers that are activated in the presence of polar solvents such as water and include materials such as n-butylcyanoacrylate. Other types of vaso-occlusive agents useful in the treatment of arteriovenous malformations include polymer solutions that coagulate by diffusion of the solvent when in contact with blood. Polyvinyl acetate dissolved in dimethylsulfoxide is one such agent. Alternatively, vaso-occlusive coils may be injected into the infusion catheter and delivered to a target site to occlude the blood flow at that site.

FIG. 4 shows a suitable catheter substrate which is guided to its intended site by the use of a guidewire rather than through the use of blood flow. As with the device described above, the catheter assembly (400) includes an elongate member (402) having a proximal end (404) and a distal end (406) and an inner lumen which extends between those two ends. It is this lumen which is to be coated with the polymeric material discussed herein to improve its lubricity. The elongate tubular body (402) has three segments; a relatively flexible distal segment (408), a relatively stiff proximal segment (410) and a transition section or middle segment (412) (separated at junction (414) from the proximal segment) between the proximal and distal segments that is less flexible than the distal segment (408) but more flexible than the proximal segment (410). Found within the lumen of the catheter assembly is guidewire (414) often having a bent tip (416) to allow ease of passage through the vasculature. The guidewire itself may also be treated with the materials discussed herein to improve its lubricity. Typically, such a catheter will have a small radiopaque band (418) of gold, platinum, palladium, or the like to permit monitoring of the catheter tip's position in relation to the tip of the guidewire or, when the guidewire is not in the catheter, to the vasculature itself. A standard proximal end fitting (420) may attached to the proximal end (404) of the proximal segment (410) often by heat fusion with reinforcing tubing. As is described in U.S. Pat. No. 4,739,768, to Engelson, the variation of flexibility may be introduced into the catheter assembly by use of sections of discrete coaxial tubing, e.g., by use of an inner stiff tube of polypropylene or high density polyethylene covered by a flexible tube of low density polyethylene or silicone in the proximal section (410) with the inner tubing junction found at (410). A thinner wall inner tubing of the same polymer as found in the proximal section (410) may be used as the inner tubing in middle section (412) to provide decreased stiffness in the middle section (412). In such an instance, the outer coaxial layer could be of the same composition and dimensions from proximal end (404) to distal end (406). Other methods of varying the stiffness to provide for strength at the proximal end, extreme flexibility at the distal end to allow conformance to the contortions of the guidewire through multiple flexions, and a middle section of strength sufficient to transmit pressure and torque from proximal end to distal end without buckling or compression. The various sections (particularly the inner section) may be tapered to provide variable stiffness through at the section or throughout the catheter.

Figure 5:
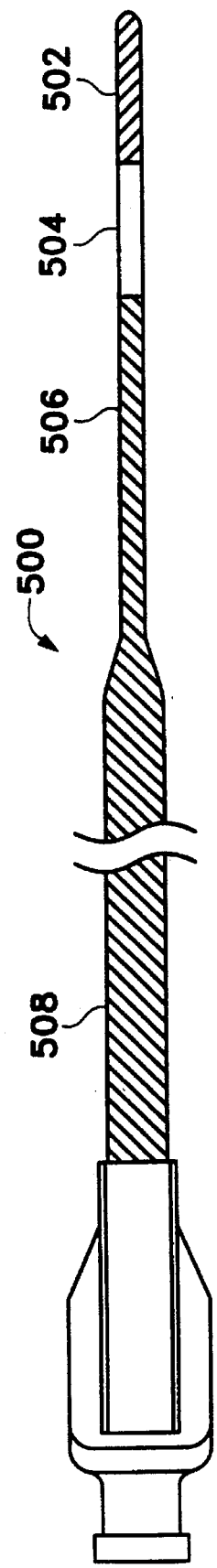
FIG. 5 is a side view of a guiding catheter made according to this invention.

FIG. 5 shows a guiding catheter (500). As was discussed above, a guiding catheter is an intravascular catheter used as the conduit for other catheters to traverse the distance between the entrance site (usually with the assistance of an introducer) at the exterior of the body to near the site where the micro-catheter is to be used. Consequently, the interior diameter of the guiding catheter is larger than the exterior diameters of the catheters discussed above. These catheters, as a group, are well known. However we have invented a guiding catheter with special properties, such properties including interior lubricious coatings as have been discussed above.

Specifically, the depicted guiding catheter (500) has a tubular body having a lumen extending from its distal end to its proximal end. Through this lumen, the interior catheter extends. The catheter depicted is formed of four generally distinct sections: the distal section (502), the intermediate section (504), the narrow proximal section (504), and the wide proximal section (508). In total, the length of the catheter is typically between 70 and 120 cm. Obviously, the number of sections in the catheter is not critical to this invention.

The distal section (502) must be reasonably stiff but of a soft material to prevent damage to the interior of the blood vessels after it is inserted and is being forwarded to its selected point. The distal section (502) is preferably of a material having a Urometer reading of 80 to 100 on the Shore "A" scale, a flexural modulus (ASTM D790) of 3000 psi to 10000 psi, and an ultimate tensile strength (ASTM D412) of at least 7000 psi. Although the guiding catheters used as substrates in this invention are suitably uv-clear, it is possible that the polymer making up this portion of the device be filled with an x-ray opaque filler such as bismuth trioxide, barium sulfate, tantalum powder, tungsten powder, or other known opacifiers.

The catheter midsection (504) preferably is of a material which forms a transition between the stiffer proximal sections (506, 508) and the softer distal section (502) both in stiffness and in size. It is often chosen of a material which is miscible or bondable with the materials in the neighboring sections. We prefer a material having a Urometer reading of 45 to 60 on the Shore "D" scale, a flexural modulus (ASTM D790) of 10,000 psi to 35,000 psi, and an ultimate tensile strength (ASTM D412) of at least 7000 psi. Our preferred materials for this portion of the device are selected from clear polyurethanes and polyether block amides (PEBA). It again possible that the polymer making up this portion of the device contain an x-ray opaque filler such as bismuth trioxide, barium sulfate, tantalum powder, tungsten powder, or other known opacifiers. For this section, we prefer barium sulfate to differentiate it from the section more distal. The inside diameter of the midsection (504) is, like the distal section (502), about 40 to 50 mils. The outside diameter of the mid-section (504) is, like the distal section (502), about 65 to 80 mils. The total length of the midsection (504) and the distal section (502) is usually no more than about 2–12 cm.

As an aside, the polyurethanes noted herein have been considered to be comparatively sticky and consequently a questionable choice for devices which must undertake sliding as a part of the device's function. The addition of the coating specified herein permits the polymer to be used in such service.

The narrow proximal section (506) is of the same general inside and outside diameter as are the midsection (504) and the distal section (502). For this and the wide proximal section, we prefer a material having a flexural modulus (ASTM D790) in excess of 90,000 psi and an ultimate tensile strength (ASTM D412) of at least 8500 psi. Our preferred materials for this portion of the device are selected from a Nylon 12 such as those sold by ATOCHEM in the Rilsan line and polyether block amides (PEBA) such as PEBAX 1147. The latter is preferred. For these sections, we prefer barium sulfate as the opacifier.

Finally, the wide proximal section (508) is made up of the same materials as is the narrow proximal section. It differs from the narrow proximal section in that it has an outside diameter of at least about 80 mils.

Another alternative of the guiding catheter involves a proximal section which is not of the two diameter version discussed above. For instance, the proximal section may be of constant diameter and produced from the polymers discussed above. The proximal section may be of a multilayer construction such as that discussed above with respect to the guidewire-guided catheter.

The interior of the catheter is coated with the same materials and in the same way as are the other catheters discussed above.

Although preferred embodiments of the invention have been described herein, it will be recognized that a variety of changes and modifications can be made without departing from spirit of the invention as found in the claims which follow.

We claim as our invention:

1. A method for producing a thin coating of a covalently bonded polymer coating on the interior of an elongated tubular member, which process comprises the steps of:

a.) supplying an elongated tubular member having an outer surface and an inner lumen which elongated tubular member is composed of a polymeric material sufficiently uv-transparent to allow cross-linking of a uv-cross-linkable polymer or oligomer on said inner lumen, b.) applying a dilute solution or suspension of a solvent and a uv-cross-linkable polymer or oligomer to the inner lumen of said elongated tubular member to form a sheet comprising said solvent and polymer or oligomer, c.) removing at least a substantial portion of the solvent from the sheet, and d.) curing said polymer or oligomer by ultraviolet radiation passing from the outer surface of said elongated tubular member to said inner lumen so to covalently bond said polymer to the lumen of said elongated tubular member.

2. The method of claim 1 additionally comprising the steps of sequentially repeating steps a.) and b.) and c.) and d.).

3. The method of claim 1 where the dilute solution or suspension comprises a solvent selected from ethers, alcohols, water, and mixtures.

4. The method of claim 3 where the solvent is selected from methanol, ethanol, isopropanol, water, and mixtures.

5. The method of claim 3 where the solution or suspension contains 0.25% to 5.0% (wt) of polymer precursor.

6. The method of claim 5 where the solution or suspension contains 0.25% to 2.5% (wt) of polymer precursor.

7. The method of claim 1 where the dilute monomer or oligomer solution contains polymers or oligomers of monomers selected from ethylene oxide; 2-vinyl pyridine; N-vinyl pyrrolidone; polyethylene glycol acrylates including monoalkoxypolyethyleneglycolmono(meth) acrylate, monomethoxytriethyleneglycolmono(meth) acrylate, monomethoxytetraethyleneglycolmono(meth) acrylate, polyethyleneglycolmono(meth) acrylate; hydrophilic acrylates such as 2-hydroxyethylmethylacrylate, glycerylmethylacrylate, acrylic acid and its salts; acrylamide and acrylonitrile; acrlylamidomethylpropane sulfonic acid and its salts; cellulose, cellulose derivatives, methyl cellulose, ethyl cellulose, carboxymethyl cellulose, cyanoethyl cellulose, cellulose acetate, polysaccharides such as amylose, pectin, amylopectin, alginic acid, and cross-linked heparin.

8. The method of claim 1 where the temperature of the solvent removal step is between 25° C. and the glass transition temperature of the polymer of the elongate tubular member.

9. The method of claim 8 where the temperature of the solvent removal step is between 50° C. and 125° C.

10. The method of claim 1 where the curing step comprises the application of ultraviolet light at a radiation density of 10 to 1200 mW/cm$^2$ to the polymeric substrate.

11. The method of claim 10 where the curing step comprises the application of ultraviolet light at a radiation density of 10 to 250 mW/cm$^2$ at a 300–350 nm wavelength to the polymeric substrate.

* * * * *